(12) United States Patent
Doraiswami et al.

(10) Patent No.: US 8,878,667 B2
(45) Date of Patent: Nov. 4, 2014

(54) WIRELESS BIOSENSOR NETWORK FOR POINT OF CARE PREPAREDNESS FOR CRITICAL PATIENTS

(75) Inventors: Ravi Doraiswami, Suwanee, GA (US); Michael G. Pecht, College Park, MD (US); Arvind Sai Sarathi Vasan, College Park, MD (US); Yunhan Huang, College Park, MD (US); Andrew Michael Kluger, San Rafael, CA (US)

(73) Assignee: Oxfordian, LLC, Dallas, TX (US)

( * ) Notice: Subject to any disclaimer, the term of this patent is extended or adjusted under 35 U.S.C. 154(b) by 517 days.

(21) Appl. No.: 13/136,069

(22) Filed: Jul. 21, 2011

(65) Prior Publication Data

US 2012/0019386 A1     Jan. 26, 2012

Related U.S. Application Data

(60) Provisional application No. 61/400,084, filed on Jul. 22, 2010.

(51) Int. Cl.
*G08B 1/08*     (2006.01)
*G01N 33/487*     (2006.01)

(52) U.S. Cl.
CPC ....... *G01N 33/48792* (2013.01); *Y10S 128/903* (2013.01)
USPC ... 340/539.12; 340/500; 340/531; 340/539.1; 340/539.11; 340/539.22; 340/539.24; 340/539.26; 340/573.1; 128/903

(58) Field of Classification Search
None
See application file for complete search history.

(56) References Cited

U.S. PATENT DOCUMENTS

| | | | |
|---|---|---|---|
| 2003/0040004 A1* | 2/2003 | Hefti et al. | 435/6 |
| 2004/0133081 A1* | 7/2004 | Teller et al. | 600/300 |
| 2007/0292956 A1* | 12/2007 | Densham | 436/2 |
| 2009/0097623 A1* | 4/2009 | Bharadwaj | 379/106.02 |

OTHER PUBLICATIONS

Arvind Sai Sarathi Vasan, Biocompatible Polymer Composite Material for Highly Sensitive Point of Care Biomems Microcantilever Sensors, Proceedings of SMTA International Conference, pp. 279-288, Oct. 2010, Olrando, Florida.

* cited by examiner

*Primary Examiner* — Curtis King
(74) *Attorney, Agent, or Firm* — Lawrence Edelman; The Law Office of Lawrence Edelman

(57) ABSTRACT

A biodegradable, bio-compatible material is described for use in wireless biosensors for point-of-care applications. The biosensor made from this biomaterial is capable of sensing environmental effects and as well as presence of bio-logical entities in the environment of concern simultaneously. Such a sensor can be used for evaluating point-of-care environmental preparedness for a specific patient through continuous monitoring of patient health performance due to environmental exposure. A two-tier network architecture is established for real-time monitoring (static case) that also provides warning of accumulated exposure. Wavelet analysis can be used to identify anomalies in the sensed data to initiate a warning.

14 Claims, 7 Drawing Sheets

WIRELESS BIOSENSOR NETWORK FOR POINT OF CARE PREPAREDNESS FOR CRITICAL PATIENTS

CROSS REFERENCE TO RELATED APPLICATIONS

This application claims priority to U.S. Provisional Application Ser. No. 61/400,084 filed Jul. 22, 2010, and entitled Wireless biosensor network for point of care preparedness for critical Patients, the contents of which application are incorporated by reference as if fully set forth herein.

FIELD OF THE INVENTION

This invention relates generally to a novel technique for monitoring the environment of a patient, and more particularly to novel monitoring devices using a biodegradable and biocompatible material, which evaluate the preparedness of an individual to a specific environment (otherwise known as Point of Care (POC) preparedness) by simultaneously monitoring both the POC environment and the individual of concern. For on-line monitoring, a two-tier network architecture is used to link the monitoring devices to a central server. Sensing changes to the ambient environment and correlating these changes with the patients' health condition, the device can signal a patient or medical care provider that the patient's environment is no longer compatible with their maintaining a healthy condition.

BACKGROUND OF THE INVENTION

Point-of-care (POC) environmental preparedness for a specific patient's medical condition has been little dealt with in the past. The study of the impact of the environment on a patient's health and subsequent deterioration of health is useful in carrying out real time (RT) survival analysis. Here by "exposure" we mean a patient's exposure to chemical or biological elements or suspended particles in the environment that are considered harmful to the specific patient and which are capable of causing degradation in the health condition of the patient.

There are two types of major categories of exposure and the proportional hazards experienced by a patient. In the first, the static case, health deterioration is caused mainly by the exposure to present environmental conditions; past exposure contributes very little in health deterioration. In the second case, the deterioration in health condition is gradual; and is due to, accumulation of effects due to past exposures to various environments.

The health monitoring condition thus needs to implement monitoring in real time and have the ability to record past exposure information. The real-time monitoring system is meant to deal with the static case exposure. In order to account for past exposure and thus the accumulation of exposure effects, a server must be used for storing health performance in the past.

A Micro Electro Mechanical System [MEMS] sensor that acts like a canary is described in our co-pending non-provisional application filed this same date entitled MEMS Barcode Device for Monitoring Medical systems at Point of Care, Attorney docket Number OX-005 US. A canary is a system or device that replicates the host system in terms of the failure mechanism and failure modes. However, the rate of degradation for the canary system is greater when compared to that of the host system, when subjected to the same environmental and operating conditions. This makes the canary fail ahead in time, thereby providing early warning of host system failure. What would thus be desirable is, to directly monitor the environment and condition of a patient in real time using "canary like" sensors.

SUMMARY OF THE INVENTION

The present invention relates generally to a novel biodegradable, and biocompatible biomaterial that can respond to various environmental factors and also satisfies property requirements of a substrate material from which bio-MEMS sensors can be built. According to the present invention, a Bio-MEMS sensor is constructed using biomaterials that can respond to various environmental factors such as temperature and humidity. By using our novel biomaterial and coating this bio-material with an appropriate bio-receptor having an appropriate actuation mechanism the biosensor can also be used to measure the concentration of bio-molecules that have a significant impact an the specific patient's health.

Changes in the environment will cause the material properties of these sensitive bio-materials to change, which can be represented by parameters such as impedance and dielectric constant. By combining biosensing and canary techniques, both the effect of environmental factors and the concentration of harmful bio-molecules can be found. Using wireless techniques along with bio-sensing capabilities, environmental conditions can be monitored and recorded by a network of biosensors, which is more useful, accurate, and robust than just one single sensor. Sensing for a particular biomolecule, the MEMS structure responds to the concentration of biomolecules in the environment by coating it with an appropriate bio-receptor and associating an appropriate transduction mechanism. Thus the combined effect of the environment and the concentration of biomolecules are studied in unison.

The sensors of this invention are well suited to be used in a networked system at the PHYsical (PHY) layer. The novel bio-material that acts as wireless sensor head, which is incorporated into a two-tier network architecture that carries health information to a server and provides feedback regarding the time over which the patient can stay in the present environment before there is a significant negative impact on his/her health.

Using a two-tier network architecture, the wireless sensor networks are deployed both in the environment (called the Environmental Sensor Network) and on the patient's body surface (called the Body Sensor Network—IEEE 802.15.6) to correlate environment and patient health information.

Wireless sensor nodes with the biomaterial in the sensor heads are deployed in the point-of-care environment which communicate changes in the material properties (which reflect environmental conditions) to a data acquisition device in its range via a wireless link In one embodiment the link can be provided using the ZigBee IEEE802.15.4 protocol, though any form of short distance wireless communication protocol can be used.

A wireless body surface network also contains our biomaterial in the sensor head deployed on the patient's body surface, providing the patient's exposure rate and health information. This data is also passed on to the data acquisition device such as a PDA (personal digital assistant).

The data acquisition device carries both types of information to a central server via mobile networks such as 3G, 4G, GPRS, or through the internet (TCP/IP). Finally, abnormal changes (anomalies) in the biomaterial parameter indicate unusual changes in the point-of-care environment that will be identified using any appropriate anomaly detection techniques.

In the case of user-oriented point-of-care testing (wherein the point of concern is a particular user) the biosensor nodes are carried with the individual wherein the biosensor material properties are recorded by a PDA, which carries the information to a central server directly via a mobile network. Our exemplary design and fabrication of a biosensor canary prototype was accomplished by optimizing the right mixture of epoxy and Carrageenan, a linear sulphated polysaccharide extracted from red seaweed; then curing, dicing and testing them. For illustration purposes, wavelet analysis was carried out on sample data signals to identify anomalies using different thresholding techniques. Further, both accelerated and in-situ tests and characterizations can be conducted to formulate the relationship between material parameter changes with those of the environment.

BRIEF DESCRIPTION OF THE DRAWINGS

So that the above-recited features of the present invention can be understood in detail, a more particular description of the invention, briefly summarized above, may be had by reference to various embodiments, some of which are illustrated in the appended drawings. It is to be noted, however, that the appended drawings illustrate only typical embodiments of this invention and are therefore not to be considered limiting of its scope, for the invention may admit to other equally effective embodiments.

DETAILED DESCRIPTION OF THE INVENTION

Biosensor Canary Design and Process

Figure 1:
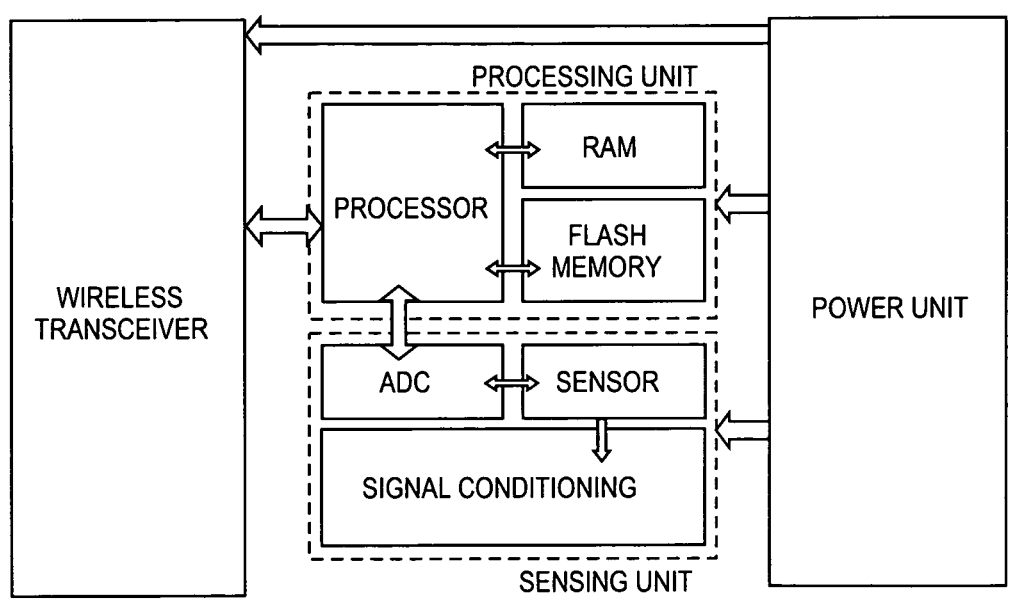
FIG. 1 is a schematic block diagram of a wireless biosensor module according to an embodiment of the invention.

The biosensor canary material of the invention is a dielectric and is integrated into a capacitor. The sensor element is designed as a parallel-plate capacitor composed of overlapping metal layers with a chemically sensitive polymer used as the dielectric (in this case the biomaterial). The capacitor design, and integration are further discussed hereinafter. The sensing circuit converts the change in capacitance to a voltage signal. The sensed voltage is converted to a digital signal, which is output to an external logic block for data processing. The passive MEMS sensor element and the sensing circuit can both be integrated on the same die.

Useful biodegradable materials include carrageenans which are large, highly flexible molecules. Carrageenans are high molecular weight polysaccharide made up of repeating galactose units and 3,6 anhydrogalactose, both sulfated and non sulfated. The units are joined by alternating alpha 1-3 and beta 1-4 glycosidic linkages. In one embodiment, the biosensors of the invention were made from carrageenans extracted from red seaweeds. These carrageenans generally take a helical shape due to their large and flexible molecular structures (which also helps them to form a gel at room temperature). The carrageenan is mixed with an epoxy, in various proportions.

In one embodiment KK-100 can be used as the biodegradable material, this material extracted from members of the class of Rhodophycease, and commercially available from Bronson & Jacobs Pty Ltd, 70 Marple Avenue, Villawood NSW 2163, Australia. In another embodiment the KK-100 Carrageenan comprises about 40-20 percent by weight of a polymer composite of epoxy and KK-100. Other optimized ratios are contemplated, and by screening, other suitable materials can be identified. For a further discussion of these hydrocolloids, reference is hereby made to the article entitled Biocompatible Polymer Composite Material for Highly Sensitive Point of Care Biomems Microcantilever Sensors, Vasan, et al., Proceedings of SMTA International Conference, pp 279-288, October 2010, Orlando, Fla. See also the article by Briones, et al., Tensile and Tear Strength of Carrageenan Film from Philippine Eucheuma Species, Mar. Biotechnol. 6, 148-151, 2004, and S-Garcia, et al., Nanobiocomposites of Carrageenan, Zein and Mica of Interest in Food Packaging and Coating Applications, J. Agric. Food Chem. 2010, 6884-6894.

In addition to being biodegradable, suitable biodegradable materials should also be biocompatible, such that there use in the presence of a patient being monitored does not expose the patient to additional environmental hazards. Carrageenans, already used as thickening and stabilizing agents in food products, have demonstrated such biocompatibility.

The effects of change in polymer permittivity cause changes in sensor capacitance. The permittivity of the selected polymer should be as high as possible for maximum sensitivity. Computational models can be used to simulate the response and sensitivity of the biomaterial to one or more surrounding environmental parameters, such as humidity and temperature. Therefore, some parameters, such as the dimensions and the shape of the biosensor can then be optimized by using various models.

The biomaterials of this invention exhibit electrical properties similar to FR4, as shown by the comparison of electrical properties at Table 1 below. Thus, this material can also be used as a low loss substrate over which electrical traces can be embedded for making electrical connections.

TABLE 1

| Material | $f_0$ (GHz) | $\epsilon'$ | tan δ | Conductivity at $f_0$ (S/m) | Attenuation (dB/inch) |
|---|---|---|---|---|---|
| FR-4 | 1.0185 | 4.47 | 0.01646 | 0.0042 | 0.1 |
| KK-100 Biomaterial | 2.53 | 3.5 | 0.0103 | 0.0053 | 0.0912 |

The materials used for the bio-MEMS sensors, possessing both good electrical and mechanical properties are also especially suitable for bio-molecule detection. These biomaterials exhibit nominal Young's Modulus of from 240 MPa to 650 MPa, such that highly sensitive bio-MEMS structures can be made. See Vasan et al., Biocompatible Polymer Composite Material for Highly Sensitive point of Care BioMEMS Microcantilever Sensors, Proceedings of SMTA International Conference, Orlando Fla., 2010, pp 279-288.

Biosensor Canary RF Network

Figure 2:
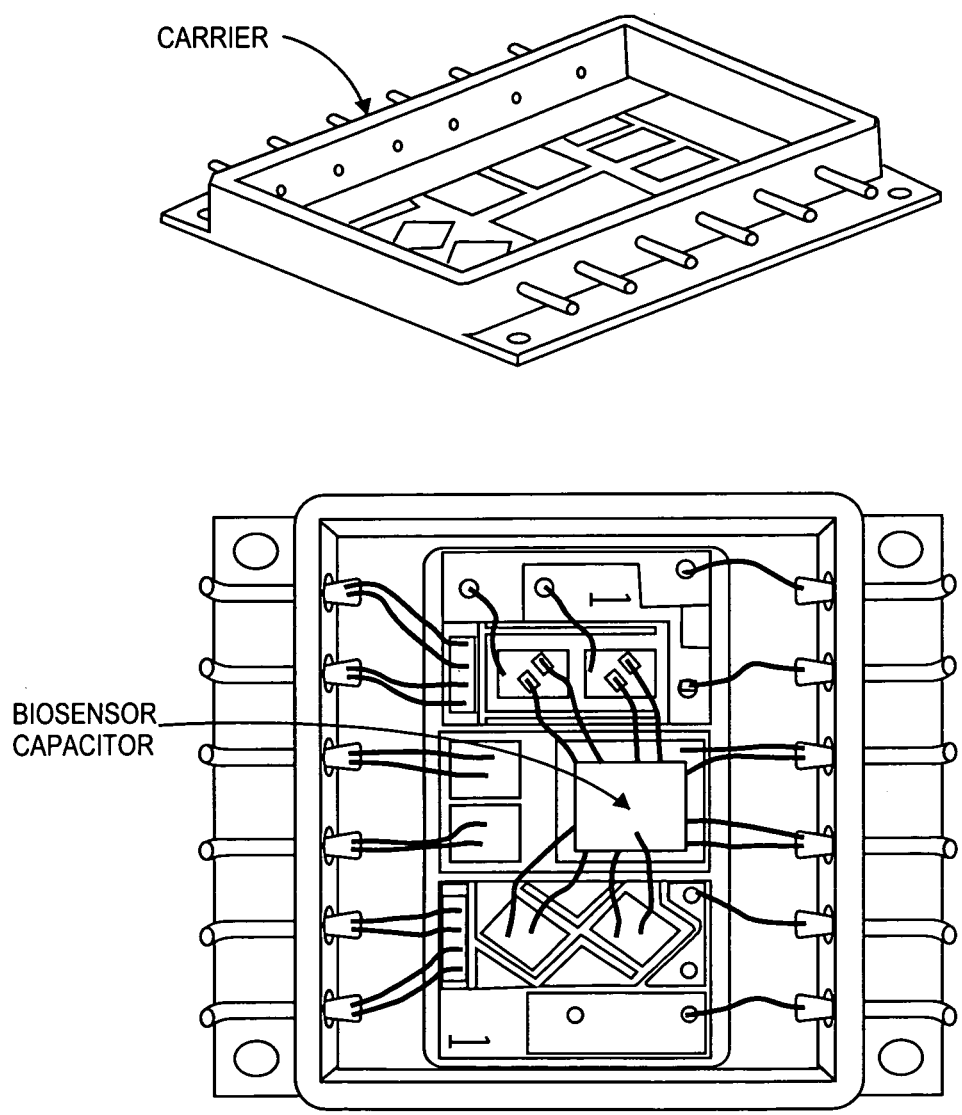
FIG. 2 is an illustration of a biosensor module, in both 3D (FIG. 2A) and top down (FIG. 2B) according to an embodiment of this invention.

The biosensor network is a collection of sensor nodes that sense changes in the environment. In our biosensor the physical parameters of the biosensor (depending on the environment) are converted into electrical signals by the transducer and correlated with human health. Deploying wireless sensor networks with our biomaterial at the sensor head allows one to identify locations that are not suitable for a particular individual or for people affected with a common type of disorder (e.g., asthma). The biosensor canary, when networked to a central server, can be useful for a point-of-care environment assessment. An exemplary biosensor module (FIG. 1) comprises the biomaterial capacitor, a processor with on-board memory, analog-to-digital converter (ADC), control circuits, signal conditioning circuits (for signal amplification, filtering, and the like) and a wireless transreceiver. A 3D and top down view of the module in its carrier is illustrated at FIG. 2.

Architecture

A central server resides at the top of this two-tier network hierarchy. The network is optimized to provide service for a large number of users and environments, and it connects to medical professionals, healthcare providers, hospitals, etc., and provides real-time information. The higher tiers for both POC environmental assessment and human physiological parameters are the same.

The lower architecture is for the following: (i) Point-of-Care Environment Assessment, and (ii) user hazard exposure.

Point-of-Care Environment Assessment

Figure 3:
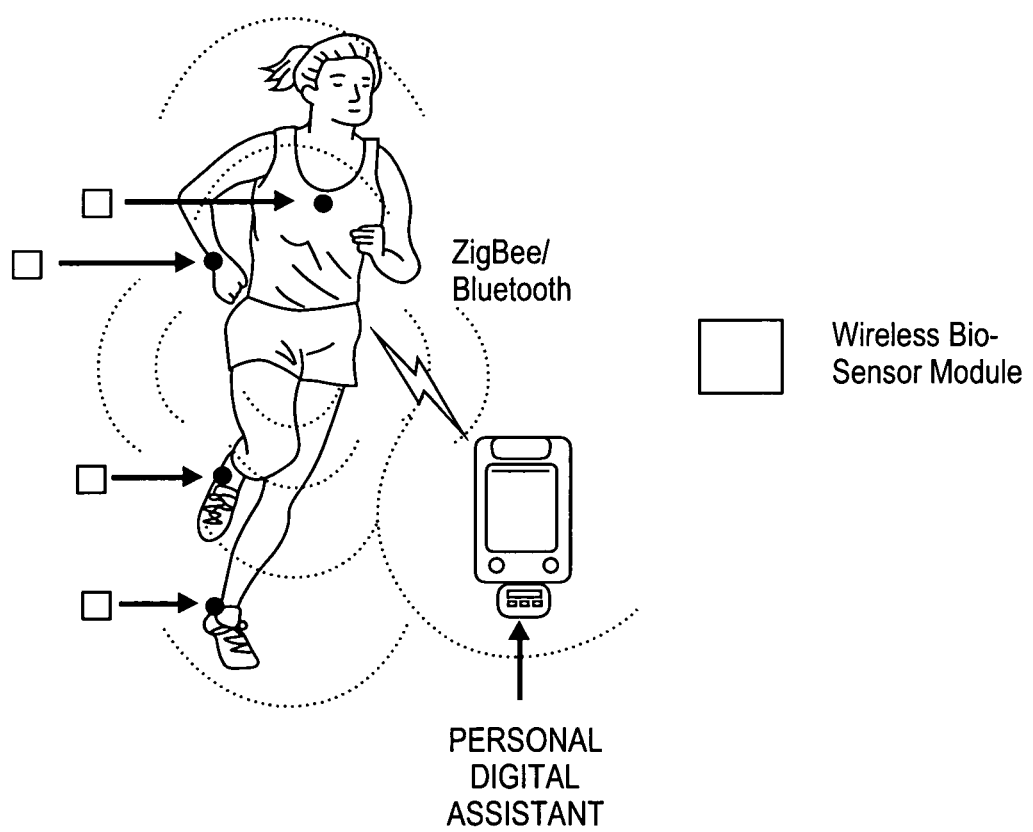
FIG. 3 includes a sketch of a lower tier architecture for user-oriented POC testing.
Figure 4:
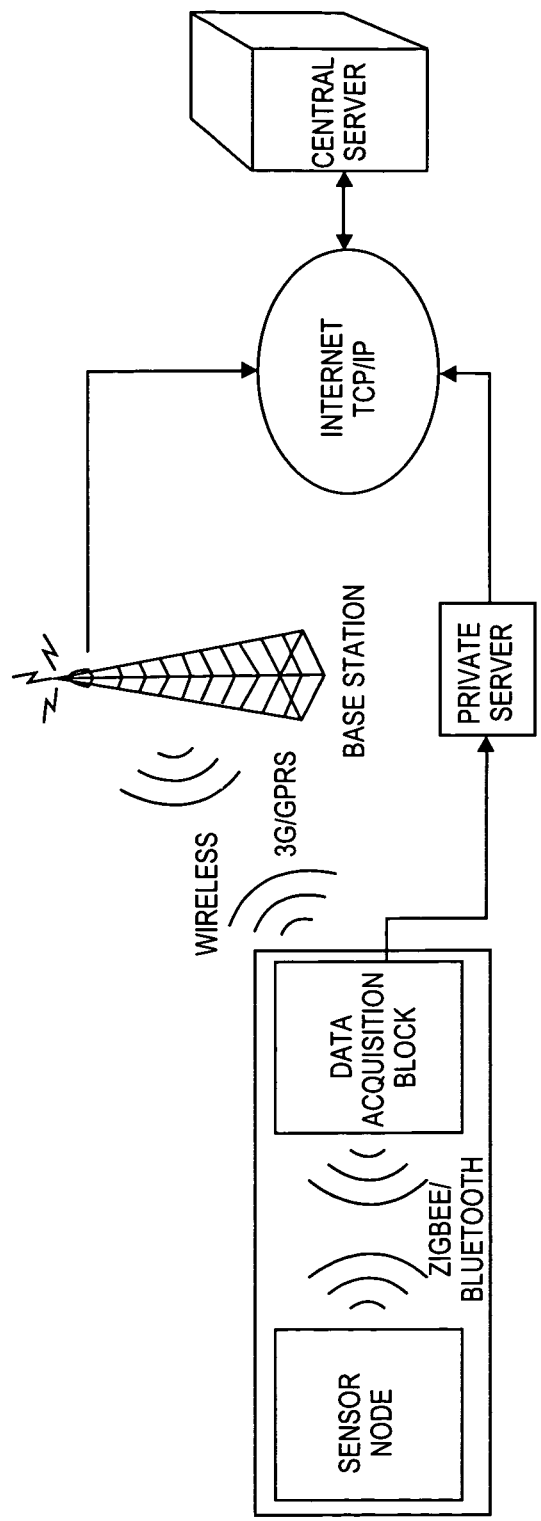
FIG. 4 is a sketch of a including both a lower tier and of a higher tier architecture.
Figure 5:
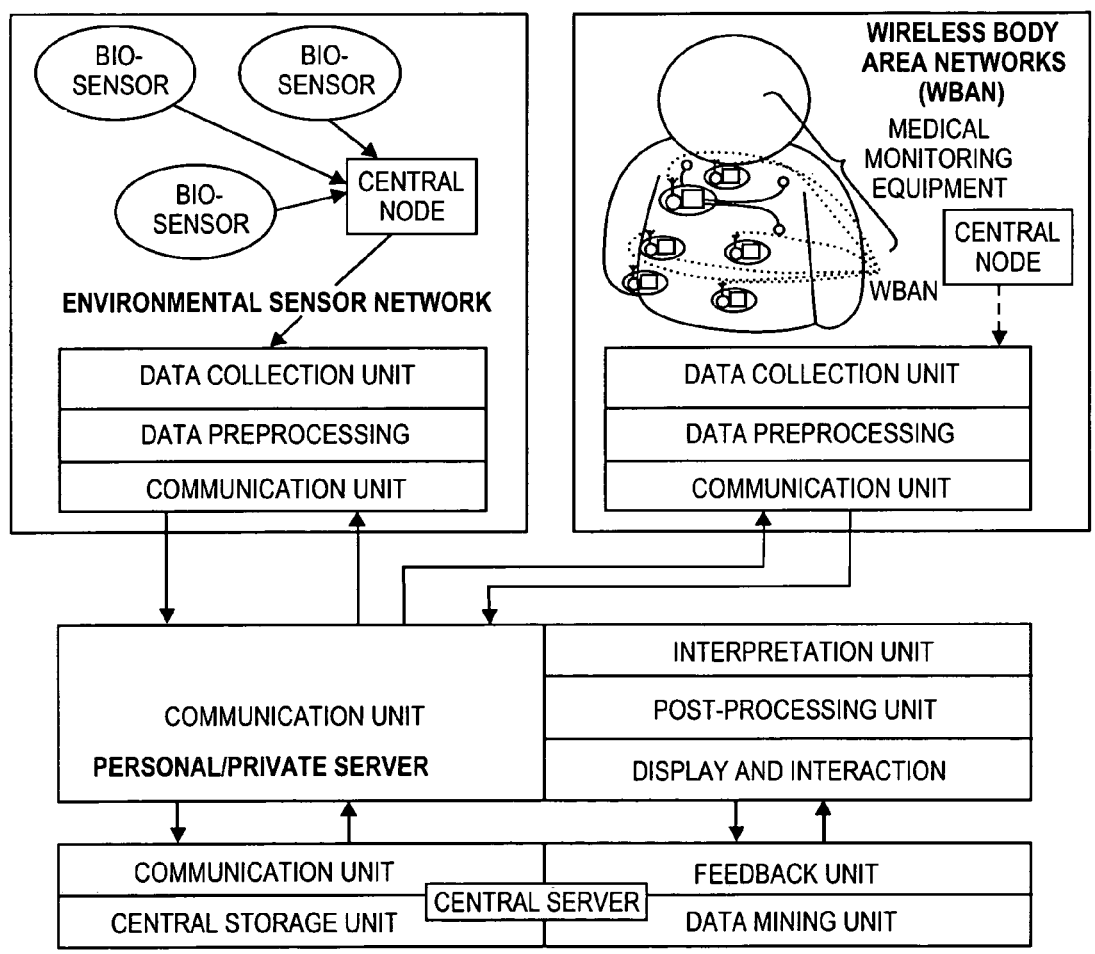
FIG. 5 is a more details illustration of a two level network architecture for point of care wireless systems.

The deployed biomaterial changes its material properties according to the physical phenomenon present in the POC environment. The control circuits, along with the ADC and processor, samples vital signals and transfers the relevant data for further processing. The data from the biosensor(s) can be transmitted in the case of a person in an outdoor environment via Bluetooth to a PDA (FIG. 3) for subsequent transmission to a central server. Or, as in the case of a patient in a fixed location such as a hospital room to a stationary data acquisition block in proximity to the sensors for subsequent transmission to a stationary data acquisition block (FIG. 4). The data acquisition block can have digital signal processing capabilities to correlate the material property changes to the change in the environmental physical phenomenon. The communication between the nodes and the environmental data acquisition device can be achieved through the ZigBee (IEEE 802.15.4), Bluetooth or any other short distance wireless protocol satisfying the requirements set forth by the IEEE 802.15 TG6 protocol. A more detailed two tier illustration of a suitable network architecture is shown in FIG. 5.

User-Oriented Point-of-Care Testing

The user to be monitored carries a wireless biosensor module. The biomaterial degrades based on environmental factors in the area immediate to the sensor. In the case of PDAs (personal digital assistants), two purposes can be achieved: 1) to segregate data from the wireless biosensor module and filter it by correlating this data with particular human parameters of concern; and 2) to communicate the decision made based on the correlation to the central server. Since PDAs have direct access to the Internet, the decision made can be directly transferred to the central server via the Internet. With only a few sensor modules, communication between the sensor nodes and the PDA can be implemented using Bluetooth technology with which a maximum theoretical data rate of 1 Mbps is achievable or with ZigBee. It should be noted that PDA can be made user-specific to analyze environmental parameters that correspond to that specific person's health condition.

Higher Architecture

The higher architecture involves the communication of the data filtered at the data acquisition block to the central server, as illustrated in FIGS. 4 and 5. This can be either wired or wireless based on the environment of application. Complex environments require further division by having their own server which in turn is connected to the global central server. For example, a hospital can have its own server wherein the entire POC environment within its locality is connected to the hospital server, which can be connected to the central global server via the Internet. In open POC environments and user-oriented POC testing, the data acquisition block connects to the central server via Mobile Networks, i.e., 3G, 4G or GPRS.

Data Analysis

In order to detect abnormal changes in the environment and classify them as suitable/not suitable for a specific patient/disorder, a data analysis module is introduced that analyzes a signal (various parameters like impedance, capacitance, etc.) as it is obtained by the data acquisition block.

Here one can make use of autonomous software that sends information in a useful format to the central server after performing data analysis. Exemplary of analysis protocols that may be used to analyze the electrical parameters obtained from the sensor (and decide if the environment is conducive or not depending on the medical condition of the patient) is wavelet analysis. Thus, wavelet analysis can be used to decompose the signal to various levels and perform local analysis to identify each of the changes. This technique also takes care of the noise that might be induced in the signals due to external factors. The choice of wavelet depends on the type of original signal analyzed and ease of implementation in the processor. Similarly, the number of levels of decomposition chosen depends on the changes that we need to detect in the signal. Other forms of anomaly detection schemes can be use, the reference to wavelet analysis cited for illustration purposes only.

The principal advantage of wavelet analysis is its ability to have time-frequency resolution. Since the signals from the biosensor will carry information pertaining to various factors like temperature, oxygen level, and humidity in the form of changes in resistance/capacitance/impedance, it becomes imperative that the each of these changes be clearly detected in the signal obtained.

Preliminary Data

Figure 6:
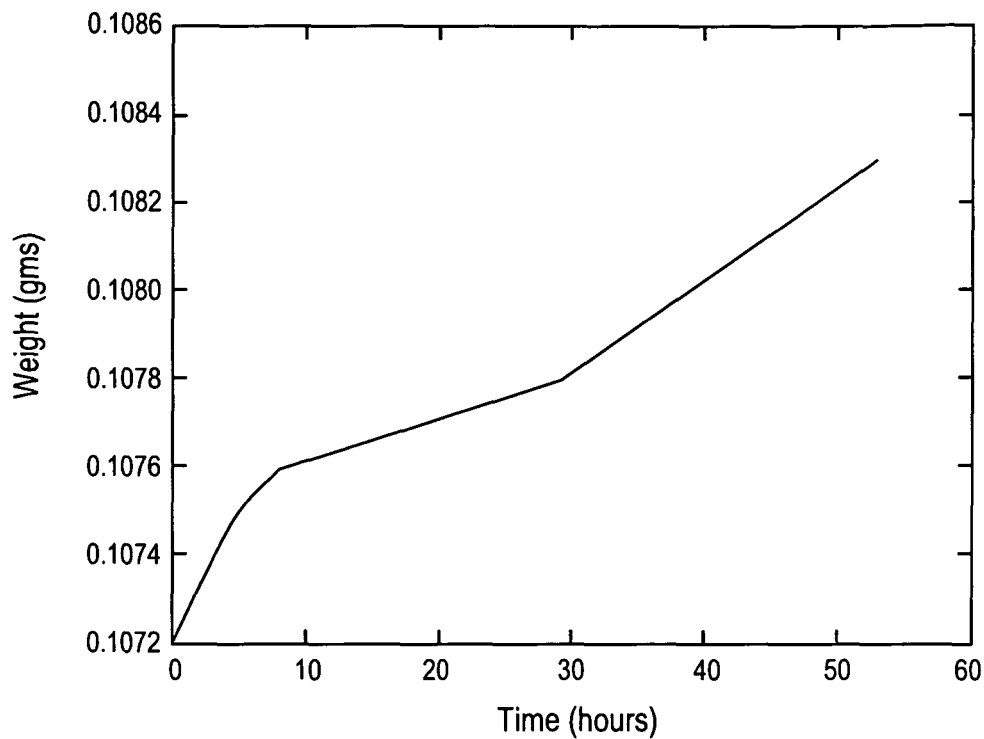
FIG. 6 is a plot of biodegradability (weight vs. exposure time) of an exemplary bio material of this invention for use in the bio-sensors according to an embodiment of the invention.
Figure 7:
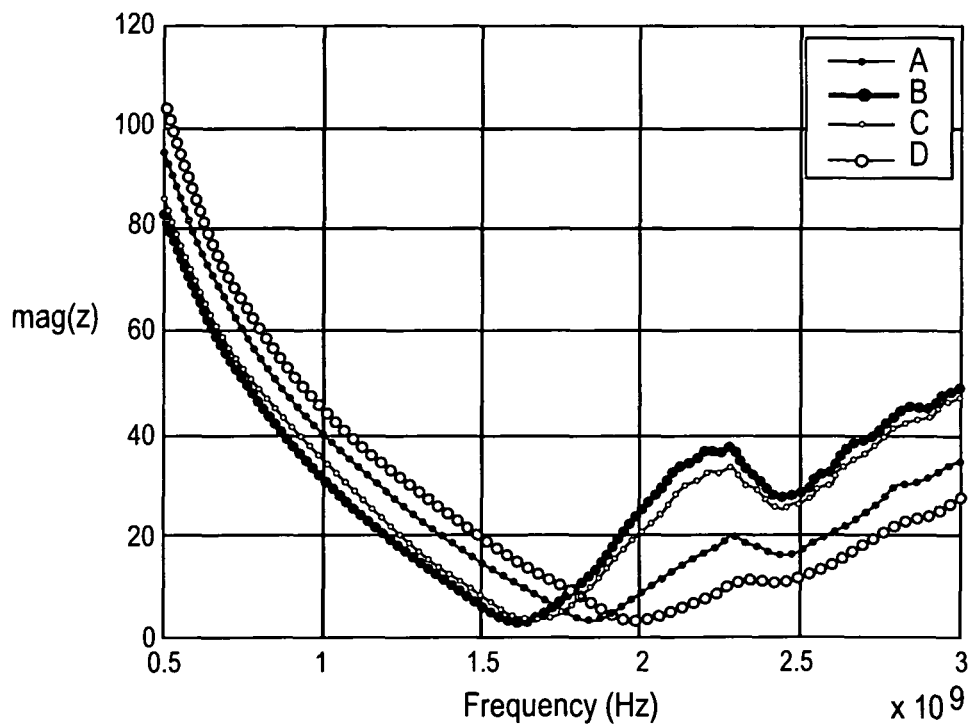
FIGS. 7 and 8 are plots, as labeled, showing how the characteristics of different biomaterials change in response to changes in the environment.
Figure 8:
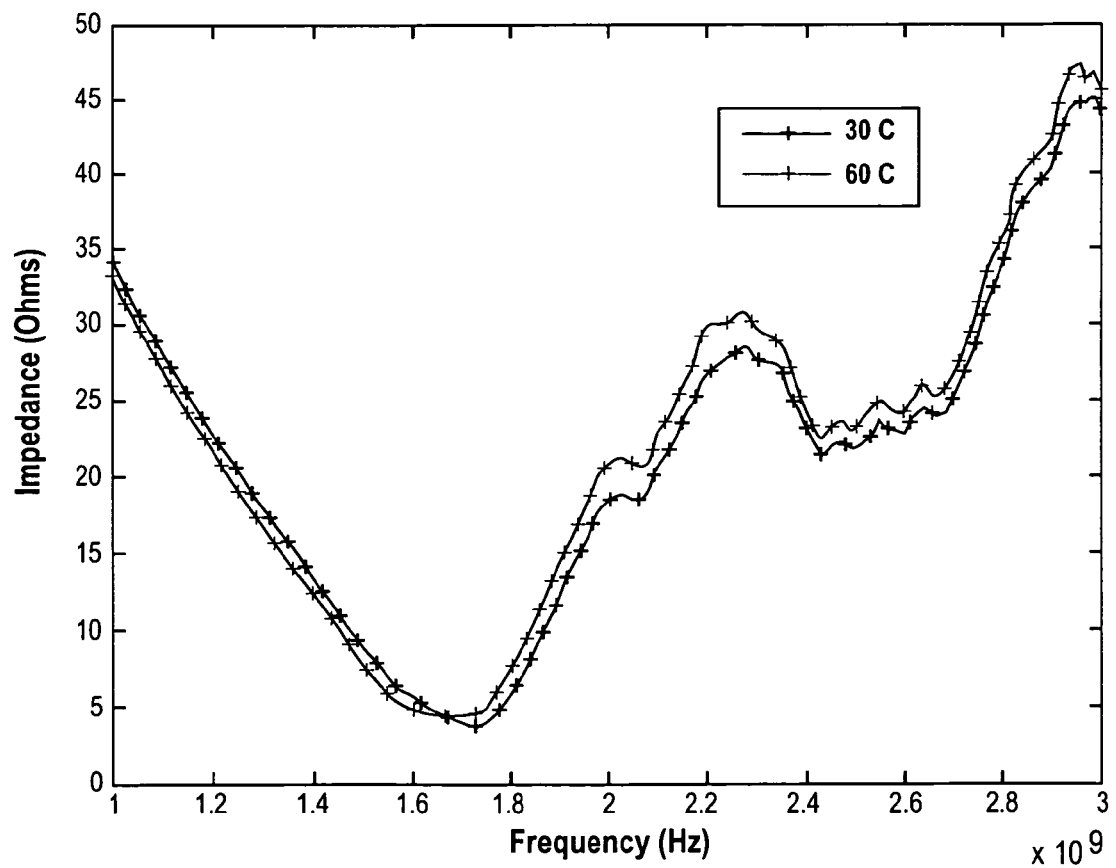

Preliminary tests were conducted to understand the bio-canary's response to changes in temperature and other environmental parameters. Biodegradability is plotted in FIG. 6, showing weight gain of the material as a function exposure time (when dipped in water). It is believed that, the material disintegrates after sufficient absorption of moisture. The collected impedance data for different composition of the biomaterial as listed in Table 2 below is plotted against frequency in FIG. 7. (Note that varying amounts of a fluorescence powder was also added to the mixture and observations of changes in fluorescence made, but not reported herein.) From the plots it is observed that as the composition varies the impedance changes gradually. In FIG. 8, the change in impedance of the material with change in temperature is shown.

TABLE 2

| Composition | Epoxy Resin (wt %) | Bio-particle (Hydrocolloid) (wt %) | Fluorescence Powder (wt %) |
|---|---|---|---|
| A | 65.60 | 24.80 | 9.59 |
| B | 74.16 | 10.79 | 14.79 |
| C | 76.55 | 7.88 | 15.69 |
| D | 79.10 | 3.41 | 17.48 |

The detection of the defined changes will result in the prediction of whether or not the environment is suitable for a particular patient. The output of wavelet analysis is transmitted to the central server from time to time. The information about the POC environment stored in the central database will help in giving real-time information about a particular room in the hospital, such as the ICU or the general ward, and also provide knowledge of whether an environment is conducive for a particular disorder (e.g., asthma) and thus help in preparing the POC environment.

While the foregoing is directed to embodiments of the present invention, other and further embodiments of the invention may be devised without departing from the basic scope thereof, and the scope thereof is determined by the claims that follow.

What we claim is:

1. A method for monitoring the environmental conditions to which an individual is exposed whereby the individual is provided with one or more biosensors, each biosensor containing a hydrocolloid material which undergoes a change in its electrical properties in response to a change in environmental conditions, said method including the steps of measuring the change in the electrical properties of the hydrocolloid material, storing said measured data in digital form in an associated electronic memory, and issuing a warning or alarm to alert the individual or a monitoring caregiver when that individual is being subjected to a change in environmental conditions which could be injurious to their health.

2. The method of claim 1 wherein said stored data periodically transmitted to a wireless transceiver which thereafter transmits the data to a central server.

3. The method of claim 1 wherein the data is transmitted to a central server via the internet.

4. The method of claim 2 wherein the data is transmitted from the one or more biosensors to a wireless transceiver via a wireless protocol.

5. The method of claim 1 wherein the hydrocolloid material comprises a carrageenan.

6. The method of claim 5 wherein the hydrocolloid material is a polymer composite containing carrageenan and epoxy.

7. The method of claim 2 wherein the central server analyses the transmitted data and correlates the changes in measured conditions to a change in an environmental condition, said environmental condition relevant to the well being of the individual being monitored.

8. A biosensor for monitoring environmental exposure, said biosensor including a capacitor in which the capacitor dielectric comprises a mixture of an epoxy resin and a hydrocolloid biomaterial, said material capable of undergoing a change in its electrical properties in response to exposure to the environment, said biosensor including means for issuing a warning or alarm to alert an individual or monitoring caregiver that the individual is being subjected to a change in environmental conditions which could be injurious to their health.

9. The biosensor of claim 8 wherein the capacitor is a parallel plate capacitor.

10. The biosensor of claim 8 wherein the hydrocolloid biomaterial is a high molecular weight polysaccharide.

11. The biosensor of claim 10 wherein the high molecular weight polysaccharide is a carrageenan.

12. The biosensor of claim 8 further including a power source, an analogue to digital converter, a microprocessor, memory and a wireless transceiver.

13. The biosensor of claim 8 wherein the mixture of epoxy and hydrocolloid biomaterial is biocompatible.

14. The method in claim 1, wherein the data is first stored in a data acquisition block.

* * * * *